United States Patent
Van Hooser

(10) Patent No.: US 8,137,615 B2
(45) Date of Patent: Mar. 20, 2012

(54) AUTOMATED WORKSTATION FOR DISINFECTING OBJECTS AND METHODS OF USE THEREOF

(75) Inventor: James Preston Van Hooser, Lynnwood, WA (US)

(73) Assignee: University of Washington, Seattle, WA (US)

(*) Notice: Subject to any disclaimer, the term of this patent is extended or adjusted under 35 U.S.C. 154(b) by 0 days.

(21) Appl. No.: 13/007,254

(22) Filed: Jan. 14, 2011

(65) Prior Publication Data

US 2011/0176961 A1    Jul. 21, 2011

Related U.S. Application Data

(62) Division of application No. 11/840,171, filed on Aug. 16, 2007, now Pat. No. 7,871,580.

(60) Provisional application No. 60/838,645, filed on Aug. 17, 2006.

(51) Int. Cl.
*A01K 29/00* (2006.01)
*A61L 2/00* (2006.01)
*A61L 2/18* (2006.01)
*A61L 9/00* (2006.01)

(52) U.S. Cl. ............... 422/28; 422/31; 422/33; 119/174

(58) Field of Classification Search ............... 119/474; 422/28, 31, 33

See application file for complete search history.

(56) References Cited

U.S. PATENT DOCUMENTS

| | | | |
|---|---|---|---|
| 3,896,768 | A | 7/1975 | Galloway |
| 5,771,841 | A | 6/1998 | Boor |
| 6,158,387 | A | 12/2000 | Gabriel et al. |
| 6,691,937 | B2 | 2/2004 | Heren et al. |
| 6,984,360 | B1 | 1/2006 | Feuilloley et al. |

FOREIGN PATENT DOCUMENTS

| | | |
|---|---|---|
| KR | 20040106815 A | 12/2004 |
| NL | 8802655 A | 5/1990 |

OTHER PUBLICATIONS

Machine Translation of KR2004/0106815 provided by KIPO, retrieved Apr. 12, 2010.*
Biomist Product Brochure, Biomist, Inc., 2007, <www.biomistinc.com>, 6 pages.
Biomist Power Sanitizing System, Presented at IFT New Products & Technologies Session, Jul. 14, 2003, 13 pages.
Press Release, "BiomistTM Power Sanitizing System to be Unveiled at IFT," Biomist, Inc., Jun. 9, 2003, 1 page.
Press Release, "BiomistTM Power Disinfecting System Kills Norovirus," Biomist, Inc., Nov. 2, 2005, 2 pages.

* cited by examiner

*Primary Examiner* — Walter D Griffin
*Assistant Examiner* — Christopher Vandeusen
(74) *Attorney, Agent, or Firm* — Perkins Coie LLP

(57) ABSTRACT

An automated workstation or apparatus for disinfecting an object in a controlled environment is provided. A method for disinfecting an object in a controlled environment is provided.

19 Claims, 20 Drawing Sheets

Cart Deck

FOOT PEDAL(S)

KNEE LEVER

CAGE LEVER / SWITCH

Hose

Assembly Guideline

360° Swivel Male Kit

Rigid Male Kit

AUTOMATED WORKSTATION FOR DISINFECTING OBJECTS AND METHODS OF USE THEREOF

CROSS REFERENCE TO RELATED APPLICATIONS

This application is a divisional of U.S. application Ser. No. 11/840,171 filed Aug. 16, 2007, now U.S. Pat. No. 7,871,580, which claims the benefit of U.S. Provisional Application No. 60/838,645, filed Aug. 17, 2006, each of which is hereby incorporated by reference in its entirety.

TECHNICAL FIELD

The invention generally relates to an automated workstation or apparatus for disinfecting an object in a controlled environment, and a method for disinfecting an object in a controlled environment, such as a specific pathogen free (SPF) environment. The workstation can reduce labor costs and reduce disease outbreaks in SPF animal facilities, SPF laboratory environments, or food processing facilities.

BACKGROUND

Specific Pathogen Free (SPF) is a general term used to indicate that certain pathogens (disease causing microbes) have been excluded from an animal or a colony of animals. SPF facilities are designed to maintain rodents (both normal and transgenic) in an environment that is free of certain infectious organisms that are pathogenic and capable of interfering with research objectives. Like all animals, rodents are susceptible to a variety of viruses, bacteria and parasites. Some of these agents are capable of inducing disease outright, while others may significantly alter host responses to experimental conditions without causing overt signs of disease. Personnel working in these facilities must adhere to strict guidelines and standard operating procedures to avoid introducing pathogens into the facility.

If a pathogen is detected, the entire animal housing room is placed under quarantine until the infected rodents are identified and removed, and successive rounds of sentinel testing demonstrate that the pathogen is no longer present. Length of quarantine depends, in part, on the type of pathogen, and how well SPF procedures were followed prior to quarantine. Depending on how widespread the pathogen is, the cost of an "outbreak" detection may exceed tens of thousands of dollars.

Specific steps must be followed closely in order to avoid contamination to the SPF environment and to research animals. Personnel may be required to put on shoe covers as they step across the threshold of the doorway into the room. In some SPF facilities (termed Barrier SPF), one must take a shower first. Once in the room, a hair bonnet, gloves and lab coat are required. To work in a dedicated hood within the room, personnel must typically put on a set of sleeves to cover their forearms and a second pair of gloves so that the gloves overlap the cuff of the sleeves.

During the transfer of an animal cage to a dedicated hood for procedural testing and/or animal husbandry (e.g., changing the bedding, water or food), care must be taken to ensure that the filter-top (i.e., micro-isolator lid) stays securely in place as it protects the inside cage environment from any airborne pathogens that could infect the animals. All items (i.e., cages, supply boxes, one's gloved hands) that go into the hood must be sprayed with disinfectant prior to their entry per standard SPF operating procedures. Once the item is sprayed with disinfectant, it may enter the hood and be placed on the work surface.

The current procedure used for disinfecting an animal cage with animals, e.g. rodents present, (and other items) is done manually by "hard-spraying" the cage with disinfectant employing a typical spray bottle, which is the standard practice worldwide. The end user holds, and carefully rotates a cage in one hand while spraying disinfectant on the external four sides, as well as the bottom, with the other "free" hand. Extreme caution must be used when rotating the cage as to avoid dropping the cage on the floor, which could potentially injure and/or kill the animal(s) inside. Note, a standard mouse cage measures 11½"L×7½"W×5"H and can house up to 1-5 animals or more (litters) while a standard rat cage measures 19"L×10"W×8"H and can house up to 3 animals or more (litters). The size of these cages alone makes them extremely difficult to handle with one hand. Once the cage has been sprayed it's extremely slippery and even more difficult to control.

The amount of time required to disinfect a single cage using the current "spray bottle method" can take up to 15 seconds or more. Rodent cages must be changed on a weekly basis by dedicated animal care staff and may also be handled on a daily basis, often multiple times, by the research investigative groups that need to perform experimental procedures. In 2006, the University of Washington (UW) alone had an annual rodent use of 193,412 (180,087 mice and 13,325 rats) with an average daily inventory of 102,718 (100,174 mice and 2,544 rats). The number of cages required to house these animals on any given day is ~40,457. The time required to ensure proper disinfecting of cages during bedding change by dedicated animal care staff alone is equivalent to ~168.5 hrs/wk or 4.2 full time employees (FTEs) (~40,457 cages×15 seconds/cage). This is a conservative estimate and does not include the time that research investigators must spend spraying down their cages prior to beginning any work in the hood. The present invention will substantially reduce the amount of time it takes to disinfect a single cage employing the "spray bottle method" as the time (duration; set to 1 second (or less) vs. 15 seconds) and volume (amount) of spray can be metered/controlled. This can be translated to a significant reduction in labor cost (~10 hrs/wk (0.25 FTE's) vs. ~168.5 hrs/wk (4.2 FTEs)).

The standard "spray bottle method" currently used globally, is time consuming, inefficient, wastes disinfectant, and increases the risk of error by laboratory personnel which may lead to possible pathogen contamination to valuable animals because one cannot ensure 100% coverage. Additionally, the spray bottle method may increase ergonomic injury due to handling slippery cages with one hand and having to repeatedly pull the trigger of the spray bottle with the other hand. Therefore, a need exists in the art to substantially reduce the amount of time required to disinfect animal cages entering a sterile hood, e.g., dedicated work space, decrease the risk of human error and increase end user handling control thereby reducing the potential for pathogen contamination and endangerment of animals and provide 100% "proof of disinfection".

SUMMARY

The invention relates generally to an automated workstation for disinfecting an object in a controlled environment, e.g., a pathogen free environment or a "clean" environment within a food processing facility, and a method for disinfecting an object in a controlled environment, e.g., a pathogen free environment or a "clean" environment within a food processing facility. The objects to be disinfected can include, but are not limited to, animal cages (with or without animals present), animal carrier, gloves, equipment, supplies, supply boxes, pens, paper, bottles, operator's gloved hands, operator's gown, or food stuff. The food stuff can be meat, poultry, seafood, shellfish, or vegetables. The pathogen free environment can be a specific pathogen free (SPF) environment, for example, in a laboratory setting. The automated system will substantially make it easier and faster to disinfect bulky cages leading to reduced time, enhanced compliance and more thorough disinfection. One advantage of the system of the invention includes reduction of ergonomic injuries to an operator due to handling of slippery cages and having to repeatedly use a spray bottle (standard process used throughout the world at the present time). Furthermore, the system increases end user handling control thereby reducing the potential for pathogen contamination and endangerment of animals (dropped cages), while in some embodiments simultaneously disinfecting worker's gloves and conserving disinfectant. The automated system and methods described herein advantageously provide reduced labor costs (70-80% of the cost for any animal facility) and can reduce disease outbreaks (which can be financially devastating to investigators) in SPF animal facilities and SPF laboratory environments globally.

An automated workstation for an end user operator to disinfect an object is provided which includes a work surface area for receiving the object. The object is typically positioned temporarily in a stationary manner in the work surface for sanitation, and the work surface can be further configured for releasing the object into a dedicated work space. The automated workstation can further include at least one spray nozzle disposed within the work surface area for spraying a microbial disinfectant fluid over an external surface of the object, a source of microbial disinfectant fluid, a fluid distribution system fluidly connected to the source of microbial disinfectant fluid, a pump connected to the fluid distribution system and a pressurization system for pumping the microbial disinfectant fluid to the at least one spray nozzle, and a control system to deliver a timed and metered amount of the microbial disinfectant fluid to the at least one spray nozzle such that the object is disinfected with the microbial disinfectant fluid. The objects can be positioned over the work surface area by an operator. Following disinfection, the object, e.g., disinfected cage, can be removed from the work surface area and moved elsewhere, for example, to the dedicated work space. The dedicated work space includes, but is not limited to, an animal bedding changing station, a laminar flow hood, a biosafety cabinet, or a clean area of a food processing facility. The object can include, but is not limited to, an animal cage with or without animals present, an animal shipping container, gloves, equipment, supplies, supply boxes, pens, paper, bottles, operator's gloved hands, operator's gown, or food stuff.

In a further aspect, an automated workstation for disinfecting an object is provided which includes a work surface area for receiving the object and releasing the object into a dedicated work space, a spray nozzle and/or nozzles positioned within the work surface area for spraying a microbial disinfectant fluid over an external surface of the object, a metered spray of a given amount and/or duration, an automated activation mechanism and/or a mechanical/physical activation mechanism, a spray nozzle and/or nozzle(s) connected by a valve and/or internal check valve to control timed and metered volume of disinfectant fluid, a manifold connecting a source of microbial disinfectant fluid to valve/spray, nozzle (s) assemblies, a fluid distribution system fluidly connected to the source of microbial disinfectant fluid, a pump connected to a pre-pressurized accumulator tank or other pressurization system, a pre-pressurized accumulator tank connected to the fluid distribution system for pumping the microbial disinfectant fluid to the nozzles, a proximity/photo-cell/IR/mechanical sensor to activate the fluid distribution system for the microbial disinfectant to the nozzles, a control system which controls a timed and metered delivery of the microbial disinfectant fluid to the nozzles such that the object is disinfected with the microbial disinfectant fluid, a power source, and an "on"/"off" switch. In one aspect, the object is an animal cage with or without animals present or an animal carrier, and the disinfectant fluid is sprayed over the external sides and bottom of the animal cage or the animal carrier, thus avoiding contact of the disinfectant spray with a cage cover or microisolator lid. In a further aspect the disinfectant fluid is sprayed over the external sides, top, and bottom of the animal cage or the animal carrier, wherein the animal cage or animal carrier has a waterproof or watertight cage cover.

The present invention further relates to the development of an automated workstation that would be used within an SPF environment. The station will permit end users to use both of their hands to hold on to the cage while quickly "scanning" it over the work surface area, misting it with disinfectant via strategically placed spray nozzles. This will reduce the amount of time required substantially to disinfect an object entering a sterile hood (i.e., dedicated work space). Additionally, the workstation will permit increased end user handling control thereby reducing the potential for pathogen contamination and endangerment to animals. The unit itself is free standing or countertop mounted and constructed of corrosion resistant materials (e.g., stainless steel, anodized aluminum, and/or plastic). It includes clean supply and "dirty" waste reservoir bottles to hold disinfectant and run-off, respectively, an electrical pressurizing pump connected to a pre-pressurized accumulator tank or pressurized reservoir, and a "work surface area" with spray nozzles strategically placed to ensure complete coverage of target areas as the cage is "scanned". The system can be activated via a proximity, mechanical, physical, or optical sensor or via a mechanical foot pedal and, knee lever, or cage lever resulting in a controlled, timed and/or metered, spray pattern of disinfectant. All working components can be connected e.g., via plumbing/tubing and electrical.

The present invention further relates to an apparatus for disinfecting an object which comprises at least one spray nozzle capable of spraying a microbial disinfectant fluid over an external surface of the object, a source of microbial disinfectant fluid, a fluid distribution system fluidly connected to the source of microbial disinfectant fluid, a pump connected to the fluid distribution system and a pressurization system for pumping the microbial disinfectant fluid to the at least one spray nozzle, and a control system to deliver a metered amount of the microbial disinfectant fluid to the at least one spray nozzle such that the external surface of the object is contacted with the microbial disinfectant fluid to reduce pathogen contamination of the object.

For a better understanding of the present invention, together with other and further objects thereof, reference is made to the accompanying drawings and detailed description and its scope will be pointed out in the appended claims.

DETAILED DESCRIPTION

Figure 1:
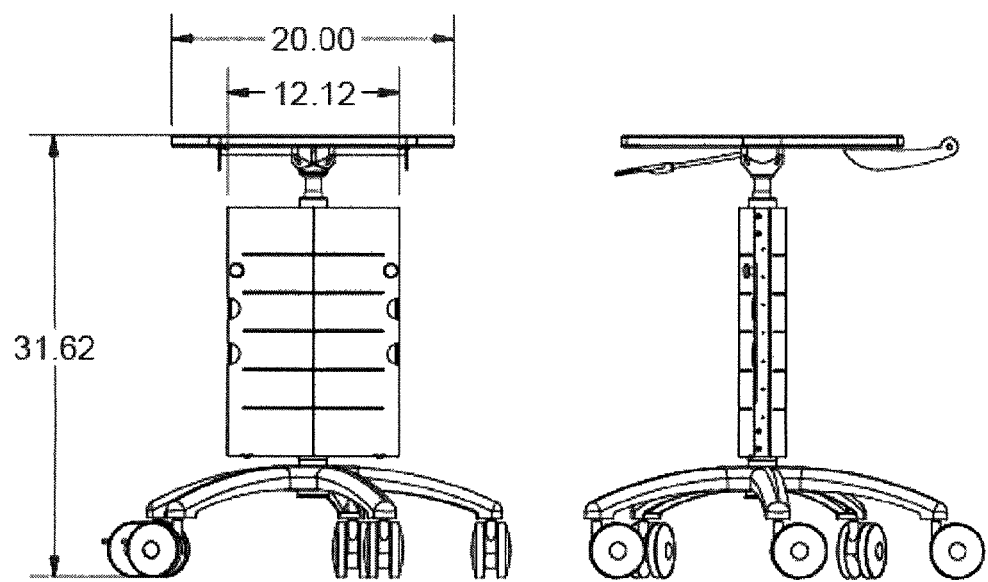
FIG. 1 is a sectional side view of an embodiment of a pneumatic height adjustable WORKSTATION/CART (to fill in dimensions) of the present invention.
Figure 2:
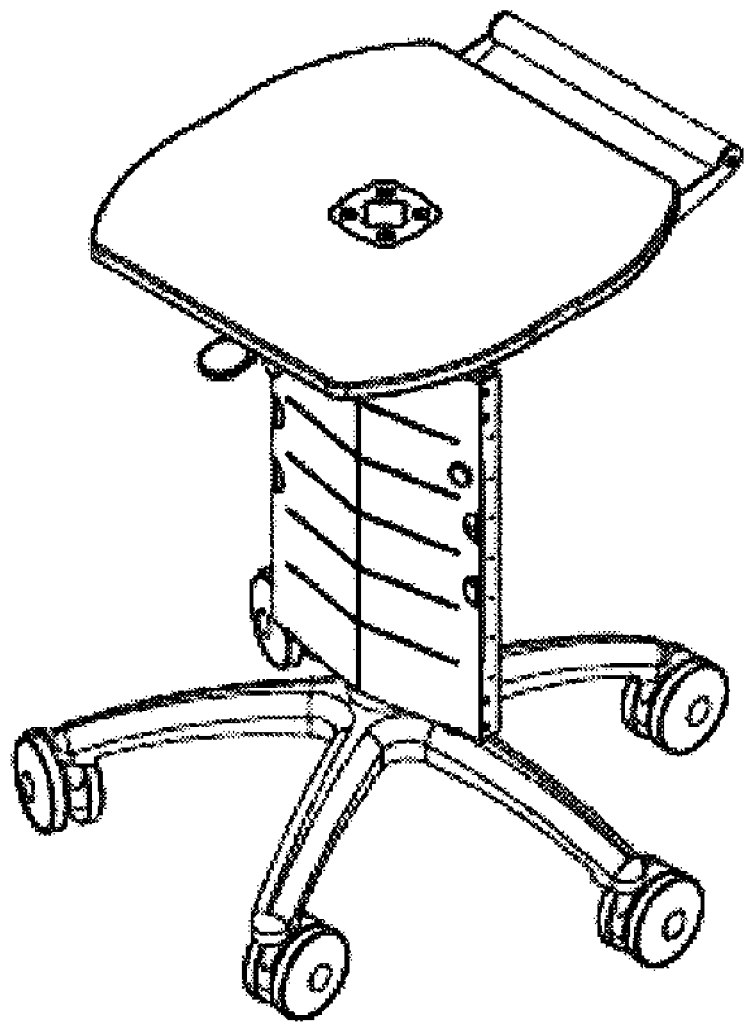
FIG. 2 is another sectional side view of the above embodiment of the present invention.

An automated system or a method to disinfect an object is provided. The system can be an automated workstation or an apparatus. The object to be disinfected typically includes, but is not limited to, animal cages with animals present, animal shipping containers, gloves, equipment, supplies, supply boxes, pens, paper, bottles, operator's gloved hands, operator's gown or food stuff. The automated workstation or the apparatus can be used in animal facilities or laboratory environments which may or may not be specific pathogen free (SPF), or in food handling facilities, as described herein below.

The automated workstation for an end user operator to disinfect an object is provided which includes a work surface area for receiving and stationary positioning of the object. The workstation can further include at least one spray nozzle disposed within the work surface area for spraying a disinfectant fluid over an external surface of the object and a control system to deliver a timed or metered amount of the disinfectant fluid to the at least one spray nozzle and further deliver disinfectant fluid to the object. The workstation can further be configured for releasably positioning the object such that the object can be moved to a separate location, e.g., into a dedicated work space, following delivery of disinfectant fluid. The workstation can further include a source of microbial disinfectant fluid, a fluid distribution system fluidly connected to the source of microbial disinfectant fluid, a pump connected to the fluid distribution system and a pressurization system for pumping the microbial disinfectant fluid to the at least one spray nozzle.

An apparatus for disinfecting an object in a controlled environment can comprise, at least one spray nozzle in a spray gun or wand capable of spraying a microbial disinfectant fluid over an external surface of the object. The apparatus comprises at least one spray nozzle capable of spraying a microbial disinfectant fluid over an external surface of the object, a source of microbial disinfectant fluid, a fluid distribution system fluidly connected to the source of microbial disinfectant fluid, a pump connected to the fluid distribution system and a pressurization system for pumping the microbial disinfectant fluid to the at least one spray nozzle, and a control system to deliver a metered amount of the microbial disinfectant fluid to the at least one spray nozzle such that the external surface of the object is contacted with the microbial disinfectant fluid to reduce pathogen contamination of the object. The spray gun or wand apparatus can be operated by a manual trigger or a pedal trigger.

A "controlled environment" refers to environments including, but not limited to, laboratories, vivaria, and laboratory animal facilities, which include specific pathogen free (SPF) laboratories, SPF vivaria, and SPF laboratory animal facilities. A "controlled environment" further refers to a food processing facility.

Specific pathogen free, or SPF, is a general term used to indicate that certain pathogens have been excluded from an animal or a colony of animals. SPF facilities are designed to maintain rodents (both normal and transgenic) in an environment that is free of certain infectious organisms that are pathogenic and capable of interfering with research objectives. A pathogen refers to a disease-causing microorganism. Pathogens or infectious agents excluded from SPF rodent facilities include, but are not limited to, mouse hepatitis virus (MHV), mouse parvovirus (MPV), minute virus of mice (MVM), reovirus-3 (Reo-3), pneumonia virus of mice (PVM), Epizootic diarrhea of infant mice (EDIM), Theiler's murine encephalomyelitis virus (TMEV), lymphocytic choriomeningitis virus (LCMV), ectromelia (mouse pox), sendai virus, sialodacryoadenitis virus (SDAV), rat parvoviruses, *Mycoplasma* pulmonis, pinworms, or fur mites. Pathogens in a food processing facility, include for example, *Salmonella*,

*Listeria monocytogenes, E. coli, Staphylococcus* or *Campylobacter* in meat and poultry processing facilities.

"Dedicated work space" refers to an SPF facility, SPF laboratory, SPF vivarium, or SPF animal facility, or an animal bedding changing station, a laminar flow hood, or a biosafety cabinet which may or may not be within an SPF facility. "Dedicated work space" can further refer to a "clean" area within a food processing facility.

The animal cage or the animal shipping container can contain one or more animals. In a detailed aspect, the food stuff can include, but is not limited to, animal, poultry, seafood, fish, shellfish, or vegetable.

Figure 14:
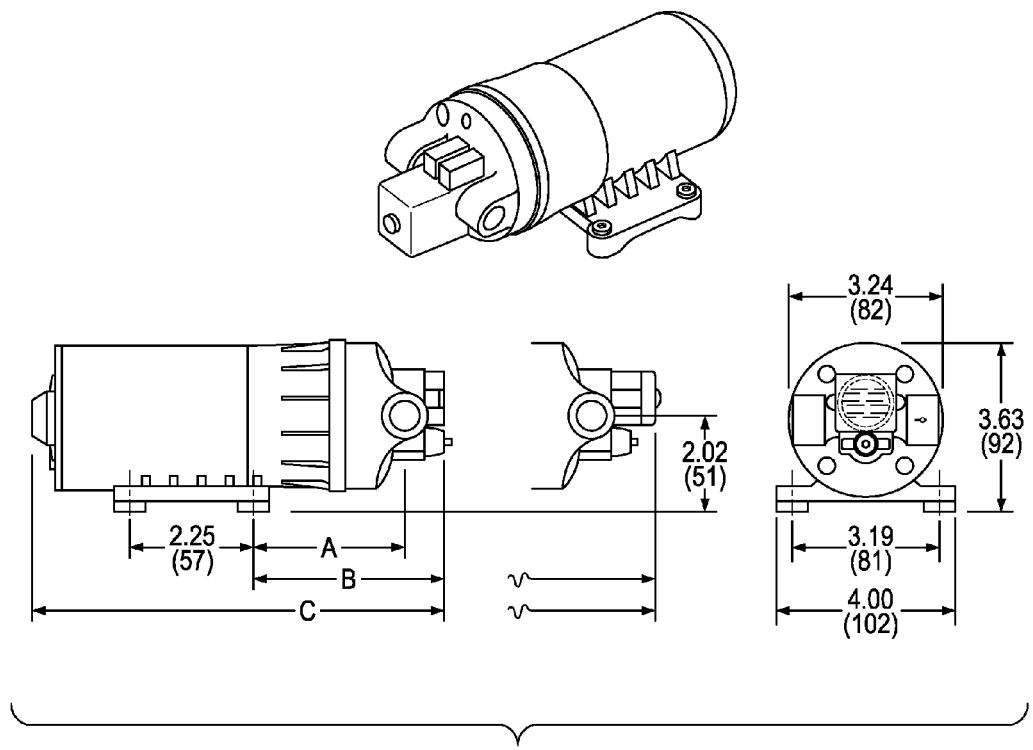
FIG. 14 is a sectional side view of an embodiment of a 12 VDC impeller type PUMP self regulated to 40-120 PSI or higher (to be determined) of the present invention.

The automated system, work station, or apparatus is connected to wall power. A unit switch is turned to "on" position. The pump (FIG. 14) draws disinfectant from the clean reservoir supply bottle (FIG. 6) and brings the system up to pressure. The pump can be designed for a wide range of applications and constructed from a selection of materials suitable for handling a broad range of chemicals. The pump is self-priming up to 8 feet (2.4 m), can run dry without damage, and made of chemical resistant materials. The pump is equipped with built-in back flow preventer, internal bypass standard, and a heavy duty ball bearing drive system. To start and prime the pump, the discharge line must be open allowing trapped air to escape thus avoiding the potential of airlock. The pressure switch will shut off the pump automatically when the discharge valve is closed and the pressure has risen to the switch OFF set point. The pressure switch will restart the pump when a valve(s) is opened and the discharge line pressure drops to the ON set point of the pressure switch. Use of a flexible hose (FIG. 21) of the correct pressure rating is used to be compatible with the fluid to be pumped. A minimum 40-mesh strainer or filter in the pump inlet line is employed to prevent foreign debris from entering the system.

Figure 9:
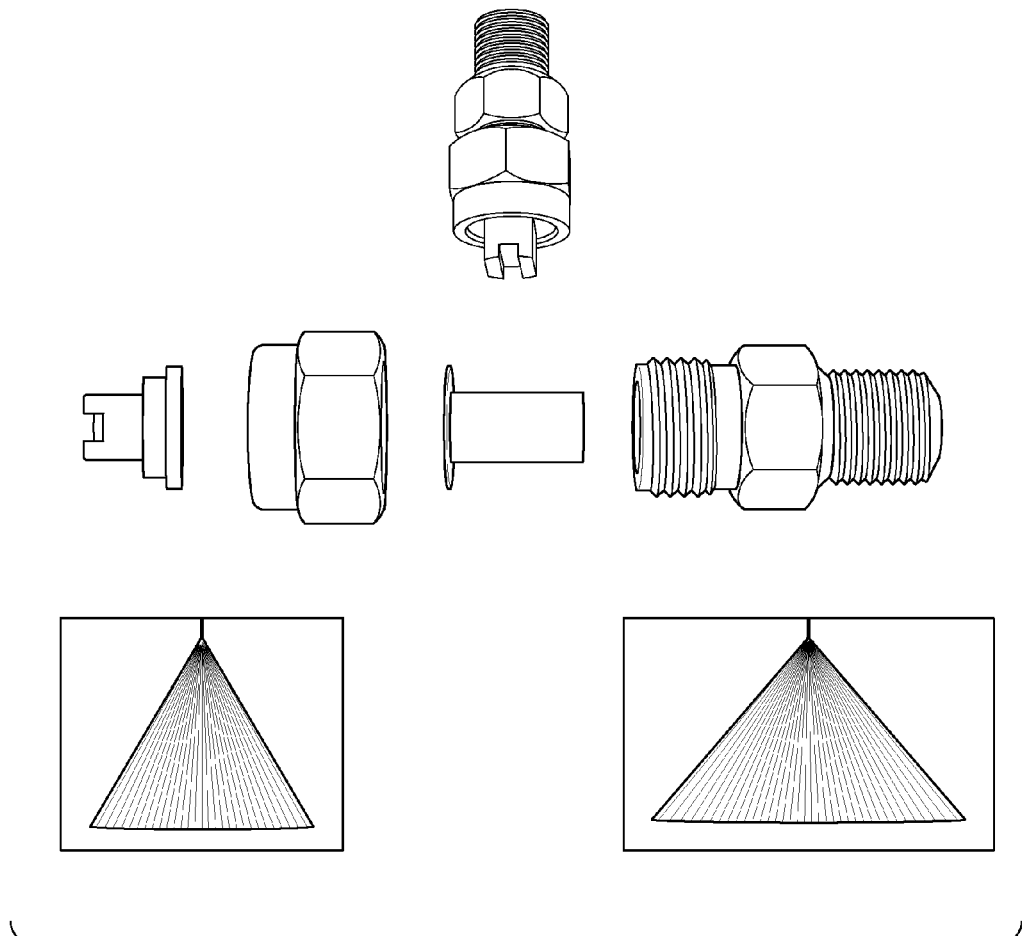
FIG. 9 is a sectional side view of an embodiment of a SPRAY NOZZLE of the present invention.
Figure 15:
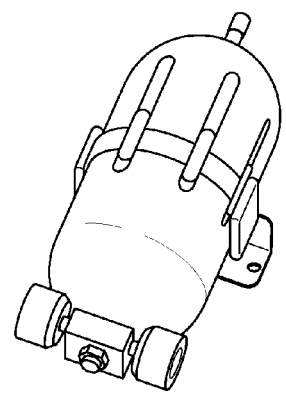
FIG. 15 is a sectional side view of an embodiment of a PRE-PRESSURIZED TANK of the present invention.
Figure 20:
FIG. 20 is a sectional side view of an embodiment of a SPRAY GUN/WAND of the present invention.
Figure 20:
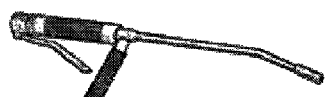
Figure 20:
Figure 20:
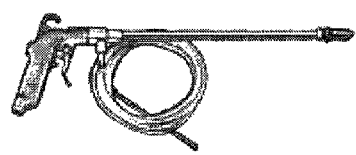
Figure 20:

At this point the pre-pressurized tank (FIG. 15), spray gun/wand (FIG. 20), spray nozzle assembly (FIG. 9), and main trunk line plumbing (FIG. 21) are at working pressure (approximately 60 PSI or higher; range 40-160). The pre-pressurized tank (FIG. 15) is a bladder type pressure storage vessel and/or pulsation dampening device designed to hold liquid (e.g., disinfectant) under pressure. The tank provides additional liquid storage to assist the pump (FIG. 14) in meeting the total demands of the system. This will extend pump life by eliminating pump pulsating on/off. The tank makes liquid disinfectant available at a moments notice without cycling the pump. The pump (FIG. 14) switches on and off to maintain this pre-set system pressure, assuring an on-demand spray pressure and supply.

Figure 16:
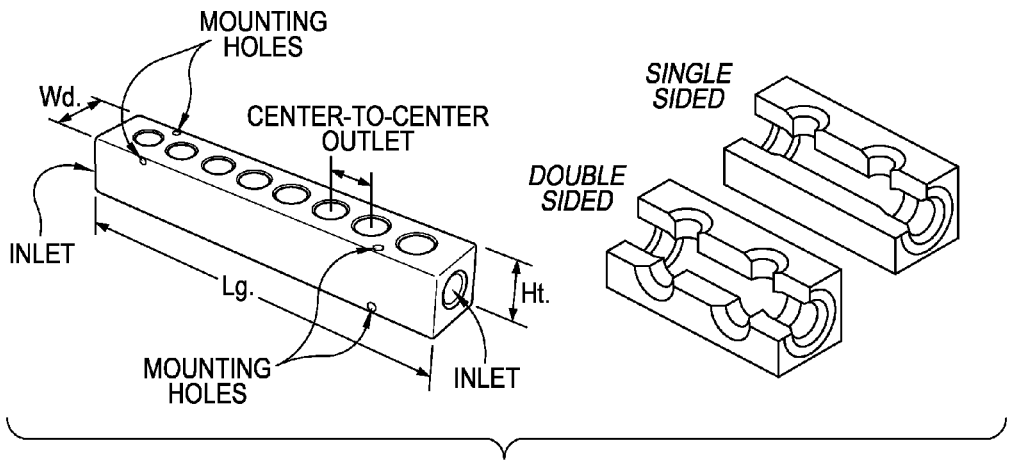
FIG. 16 is a sectional side view of an embodiment of a MANIFOLD of the present invention.
Figure 17:
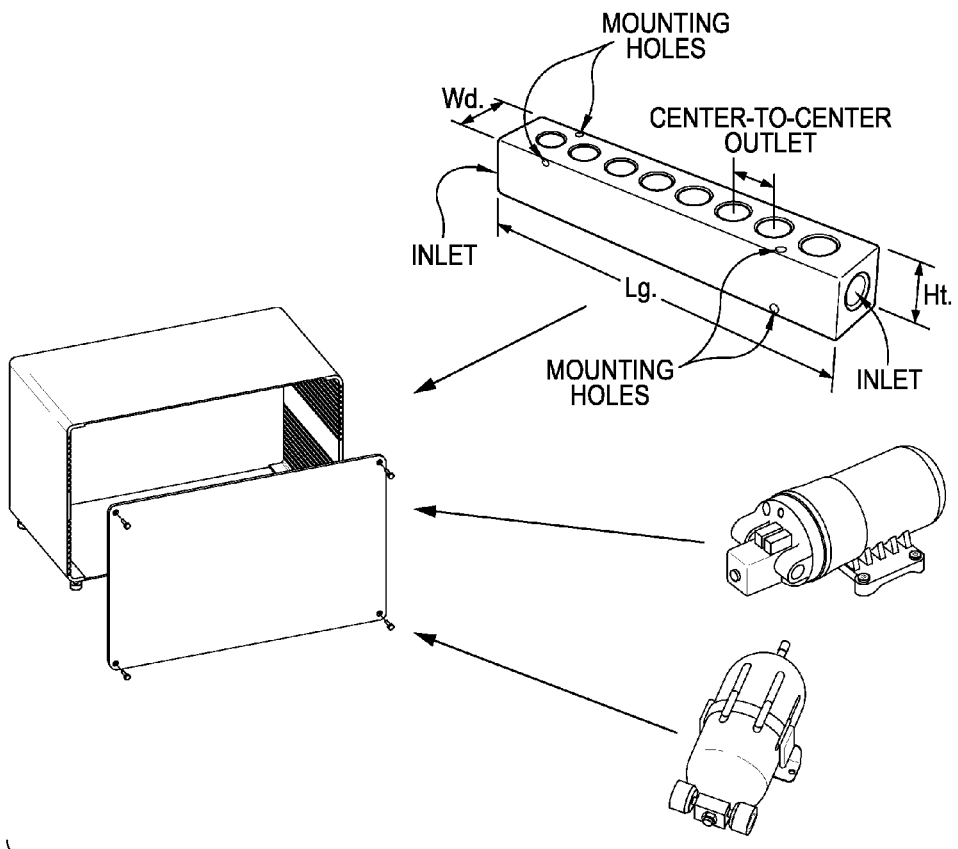
FIG. 17 is a sectional side view of the above embodiments of the present invention within the PUMP ENCLOSURE (FIG. 5).
Figure 18:
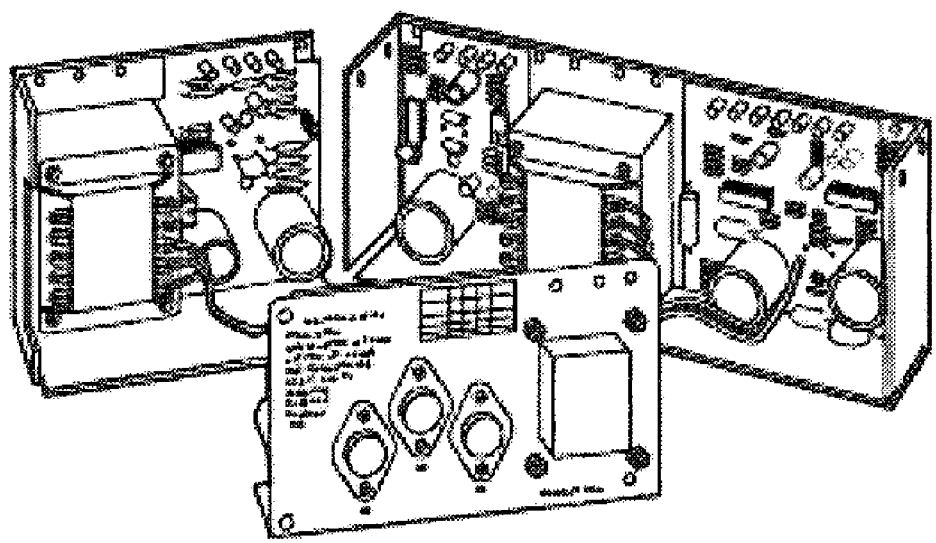
FIG. 18 is a sectional side view of an embodiment of a POWER SOURCE and/or SOURCES/POWER SUPPLY of the present invention.
Figure 19:
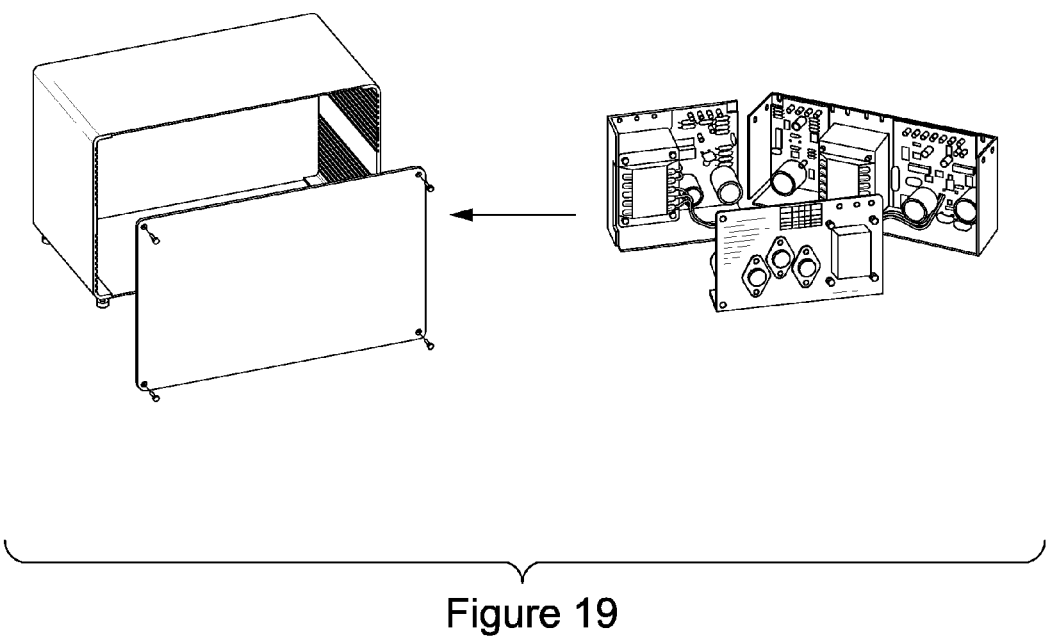
FIG. 19 is a sectional side view of the above embodiments of the present invention within the POWER ENCLOSURE (FIG. 5).

The main trunk line plumbing (FIG. 21) is joined via a manifold (FIG. 16), creating a common location to organize multiple lines (FIG. 21) within the fluid system. The manifold is employed to distribute liquid (i.e., disinfectant) to multiple individual spray nozzle(s) (FIG. 9), connected to micro-solenoid valve(s) (FIG. 10), via threading the fittings to one source. A central distribution point makes maintenance easier. The manifold can have two inlets (one at each end) and 2-10 mounting holes and be made of corrosion and chemical resistant materials.

The main trunk line plumbing (FIG. 21) can include, but not be limited to, the following materials, shape and reinforcement (respectively): acrylic, blended PVC/polyurethane, butyrate, ethylene tetrafluoroethylene, ethyl vinyl acetate, nylon, polyethylene, polypropylene, polytetrafluoroethylene, PVC, PVDF, Teflon® polytetrafluoroethylene, Tygon® high purity, Tygon® tygothane polyurethane, Tygon® PVC, nitrile; single line and self-retracting coil; and un-reinforced, braid-reinforced, wire reinforced or braid covered.

The spray gun/wand (FIG. 20) can be manually activated at any time by the user via a trigger switch. The purpose of the spray gun is to allow the end user to manually disinfect, wash down, rinse, and/or general cleanup of the SPF facility/room and/or laboratory environment or food processing facility, including a dedicated hood, floor, and the unit itself. The spray gun/wand will include a front/rear trigger, a high-pressure angled spray nozzle, a trigger lock that prevents accidental discharge and a trigger guard that protects the trigger from damage. The spray gun/wand can be lightweight and corrosion resistant. The gun/wand will be equipped with a swivel inlet connector for easier gun handling and to prevent hose (FIG. 21) from kinking.

Figure 10:
FIG. 10 is a sectional side view of an embodiment of a stainless steel direct acting solenoid VALVE (to be determined) OR equipped with an internal check valve (to be determined) either or both in line between nozzle tip and pressurization system of the present invention.
Figure 24:
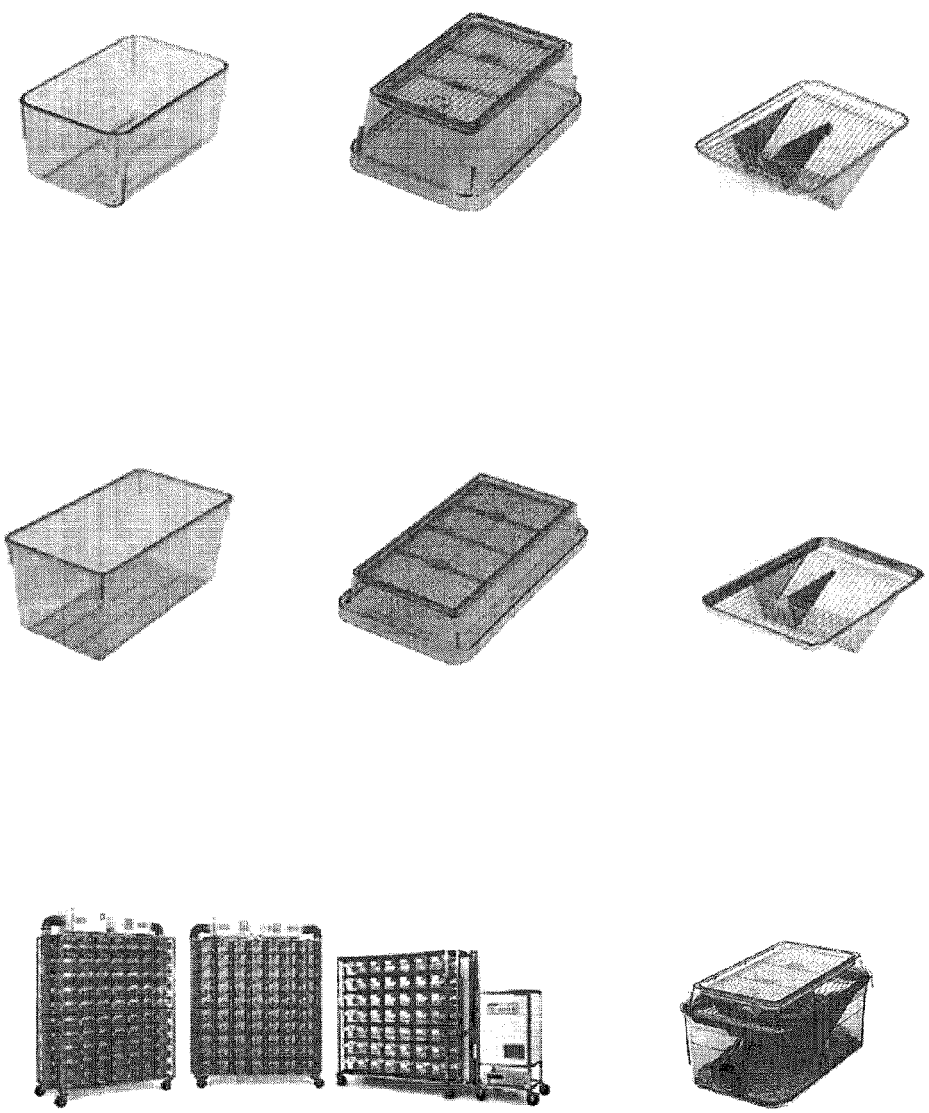
FIG. 24 is a sectional side view of an embodiment of the CAGE(s). detailed description

The presence of a cage (FIG. 24) is detected by a sensor: photo-cell, proximity (via cage switch frame), optical, infrared (IR) (FIG. 11), and/or via manual mechanism: e.g., mechanical physical (FIG. 13) (manual override) which triggers the opening of the spray nozzle(s) (FIG. 9) via solenoid valve(s) (FIG. 10) and/or spring loaded internal check valve (FIG. 10). The sensors will detect an object without physical contact. They often emit an electromagnetic field or beam and look for changes in the field via object-reflecting style, reflector style, or two-piece style (refer to FIG. 11). The object (e.g., animal cage) being sensed is referred to as the sensor's target. An optical sensor is common in position and motion sensing. The animal cage passes between an LED and detector to interrupt a light beam or an IR sensor. An IR sensor works by sending out a beam of IR light, and then computing the distance to any objects from characteristics of the returned (reflected) signal.

Figure 3:
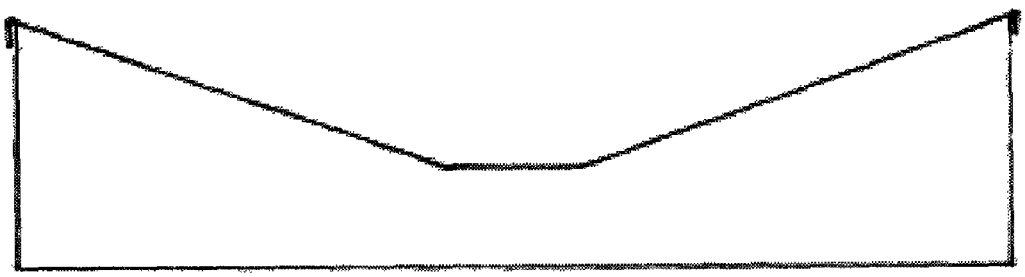
FIG. 3 is a sectional side view of an embodiment of a SPRAY WORK SURFACE AREA/RETURN DRAIN PAN (to fill in dimensions) of the present invention.
Figure 4:
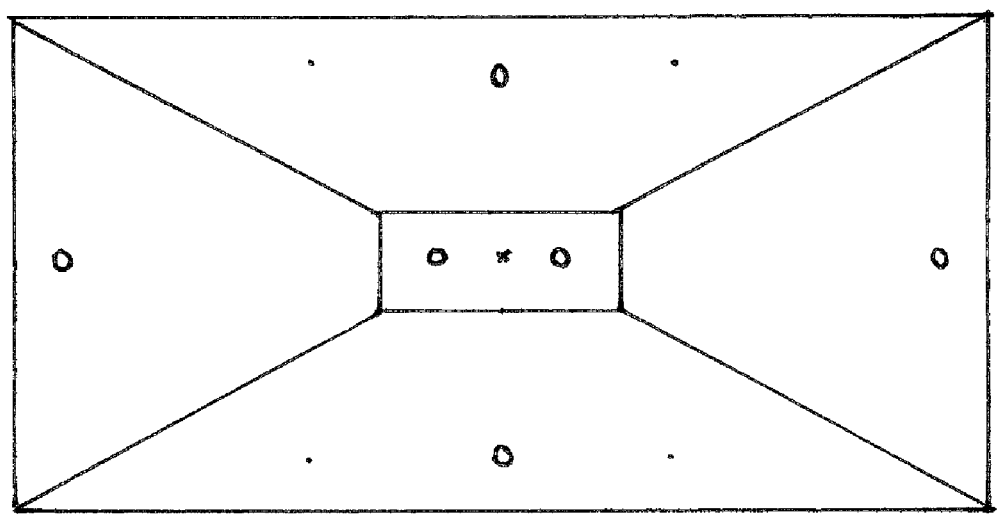
FIG. 4 is a top view of an embodiment of a SPRAY WORK SURFACE AREA/RETURN DRAIN PAN (to fill in dimensions) of the present invention.
Figure 5:
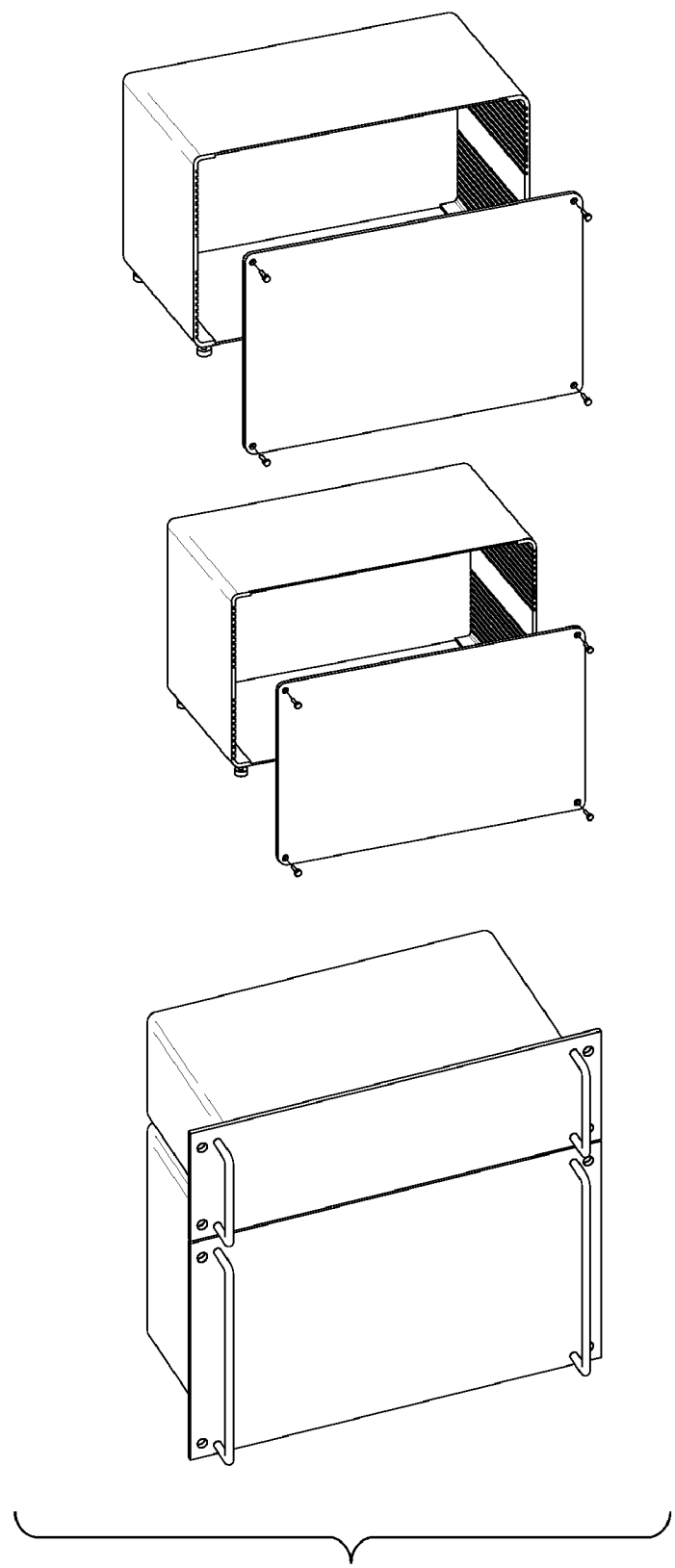
FIG. 5 is a sectional side view of an embodiment of a corrosion resistant PUMP/POWER ENCLOSURE(s) (to fill in dimensions) of the present invention.
Figure 21:
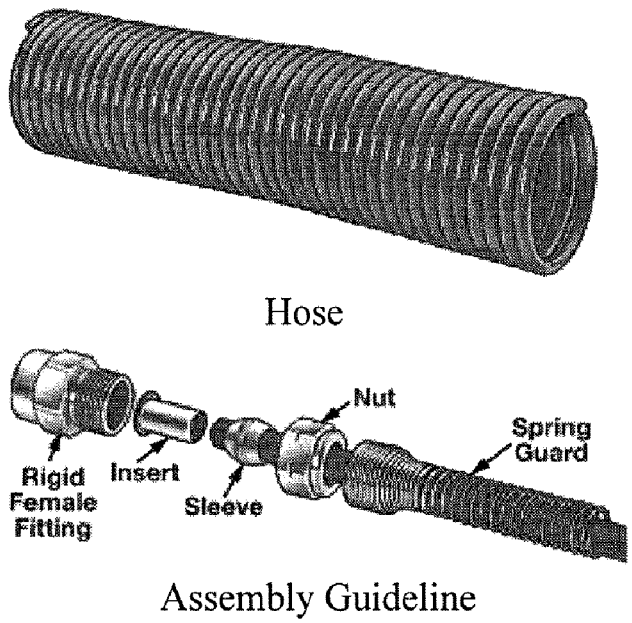
FIG. 21 is a sectional side view of an embodiment of the PLUMBING/TUBING of the present invention.
Figure 21:
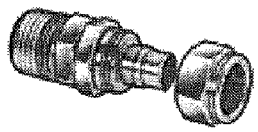
Figure 21:
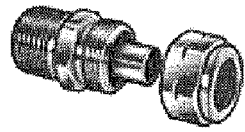
Figure 21:
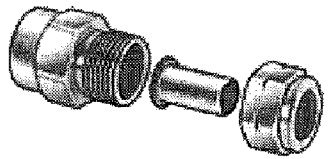

A timed (duration) and/or metered volume (amount) of disinfectant is initiated when a cage is "sensed" via a "object-reflecting", "reflector", "two-piece style" sensor OR manually via secondary actuator (FIG. 13), which causes the solenoid valve(s) (FIG. 10) to open the spray nozzle(s) (FIG. 9) disposed within the work surface area (FIG. 3—sectional side view only; FIG. 4—top view only; and FIG. 12—sectional side view of embodiments FIGS. 3, 9, 10, 11, and 24) thereby misting the external four sides and bottom surfaces of the cage (FIG. 12, 24) (e.g., target area). FIG. 12 shows a standard mouse cage in position (end user, using both gloved hands, holds cage in fixed position) being sprayed/misted with disinfectant. FIG. 3 represents a side view of the work surface area/return drip pan made of corrosion and chemical resistant material. FIG. 4 is a top view of the work surface area/return drip pan. The spray nozzle(s) are strategically placed/disposed in the two sides and ends of the work surface area. Any disinfectant that drips off the animal cage after a timed and metered volume of disinfectant is collected to the waste reservoir bottle (FIG. 6) via line pluming (FIG. 21).

Figure 6:
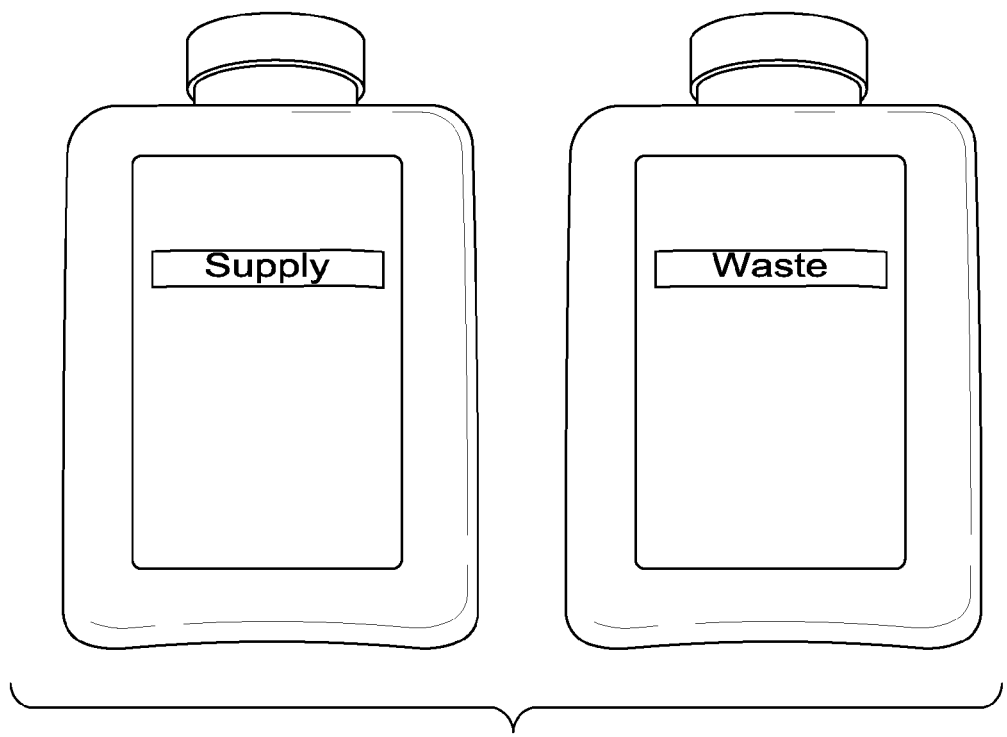
FIG. 6 is a sectional side view of an embodiment of a CLEAN/WASTE RESERVOIR BOTTLE (to fill in dimensions) of the present invention.
Figure 7:
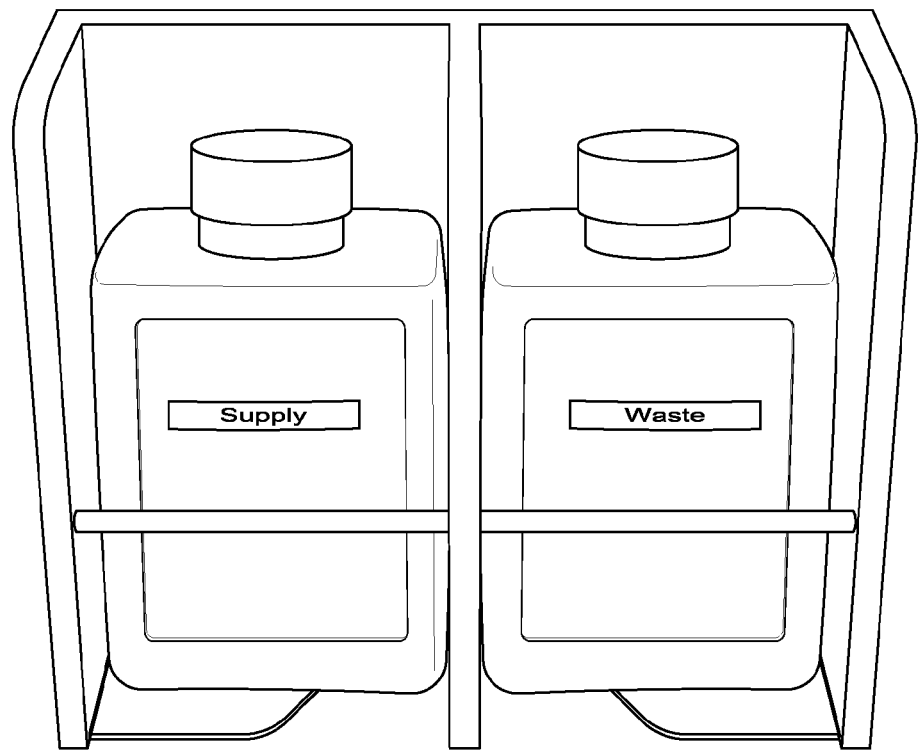
FIG. 7 is a sectional side view of an embodiment of a CLEAN/WASTE RESERVOIR BOTTLE SYSTEM (to fill in dimensions) of the present invention.
Figure 8:
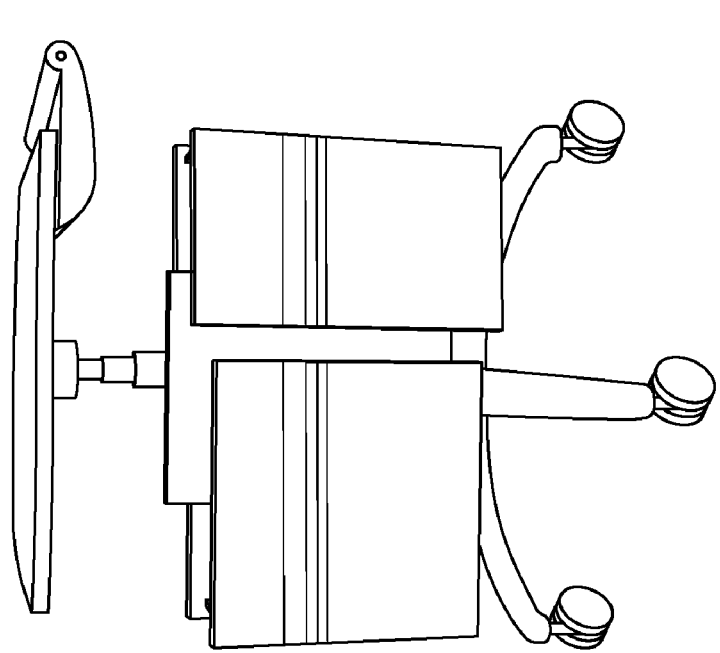
FIG. 8 is a sectional side view of the above embodiments of the present invention (FIG. 5, 6, 7).
Figure 8:
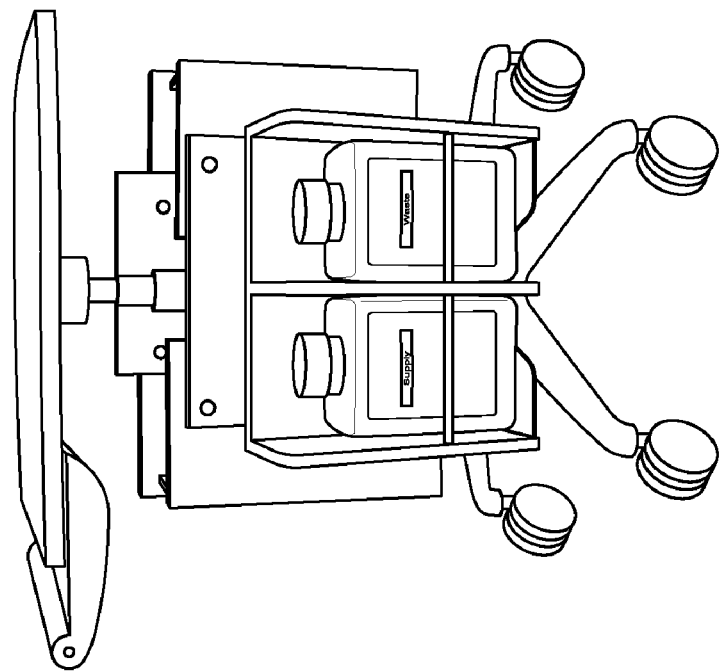

At the end of the pre-determined time (duration) and/or volume (amount), the spray nozzle(s) (FIG. 9) shut-off, thereby terminating the flow pattern of disinfectant (FIG. 9) from the clean reservoir supply bottle (FIG. 6). The spray nozzle(s) may have interchangeable spray tips and optional nozzle strainer equipped with stainless steel (corrosion resistant) screens of various mesh sizes. The nozzle(s) will have optional spray patterns to include but not be limited to: flat fan; fan, full cone, square full cone, full cone with uniform distribution, dense full cone, fog, and straight jet; adjustable from 0-110 degrees, and spray volume of 0.011 to 101 L/min).

The cycle is repeated by recognizing the presence of another cage (FIG. 24) via the photo-cell/proximity/optical/

Figure 11:
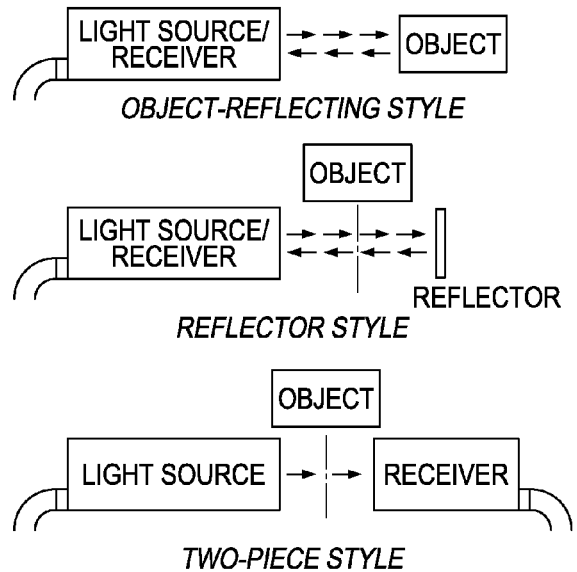
FIG. 11 is a sectional side view of an embodiment of a SENSOR and or SENSORS (plural) of the present invention.
Figure 11:
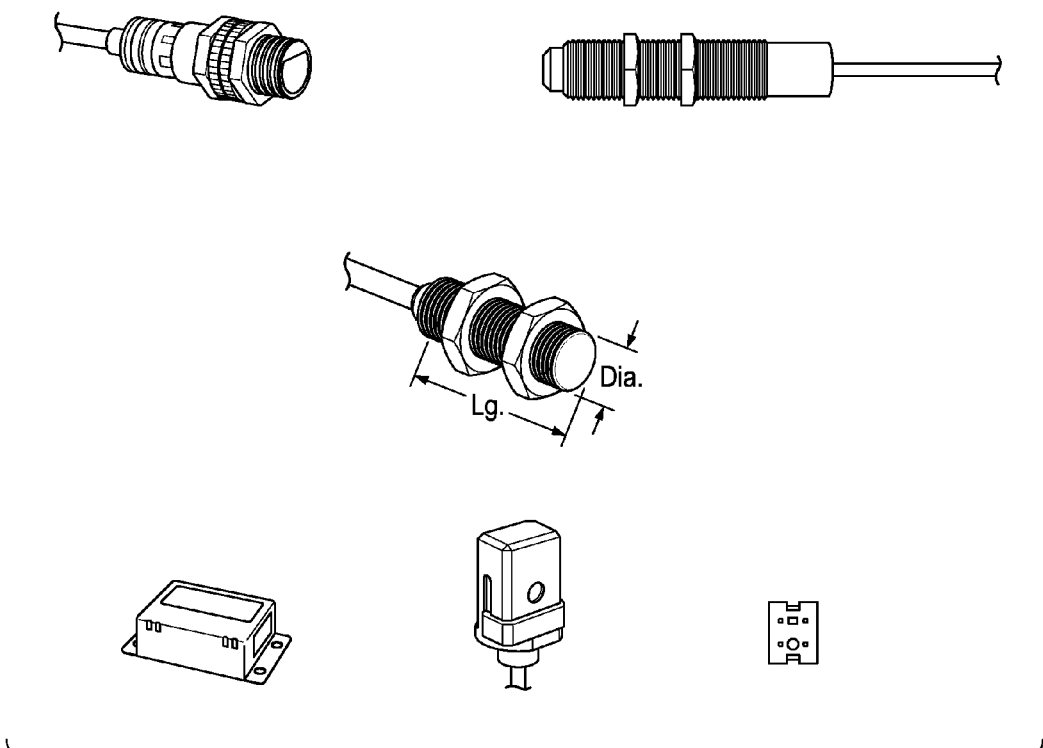
Figure 12:
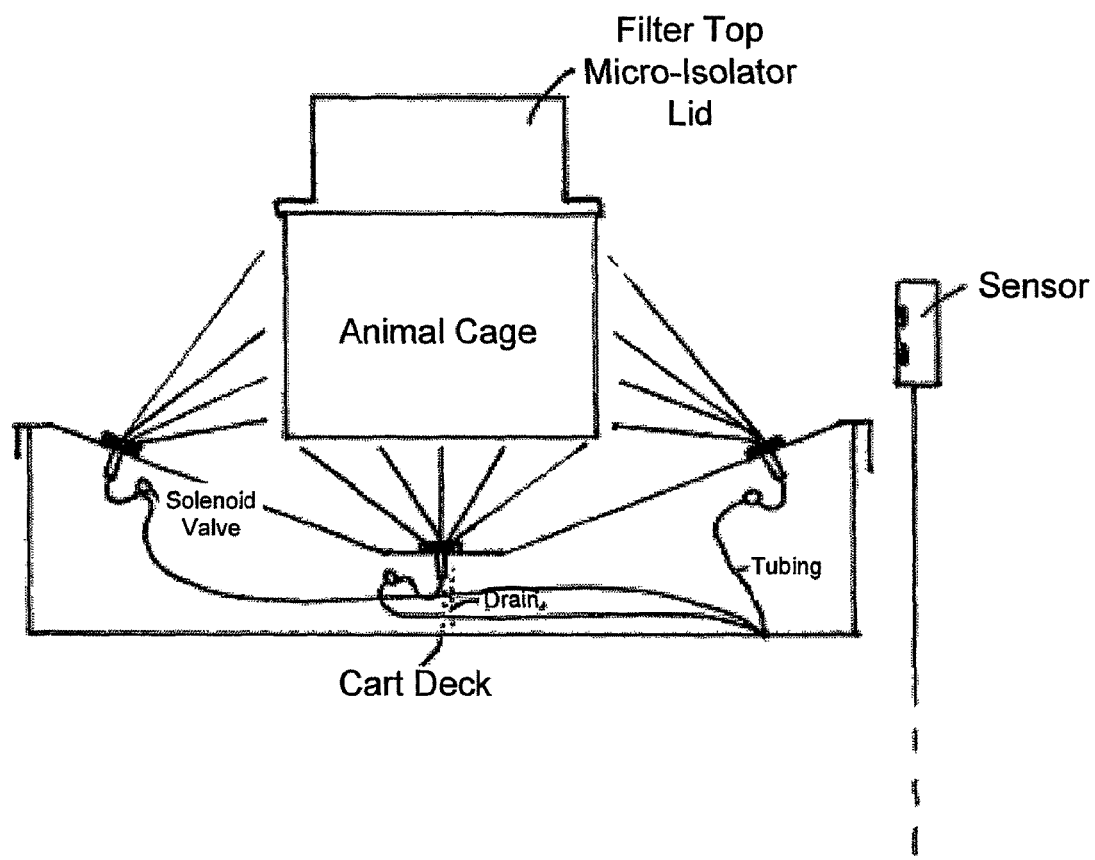
FIG. 12 is a sectional side view of the above embodiments of the present invention disposed within the work surface area (FIG. 3, 4).
Figure 13:
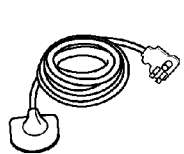
FIG. 13 is a sectional side view of an embodiment of a primary or secondary actuator FOOT PEDAL and/or KNEE LEVER and/or CAGE LEVER of the present invention.
Figure 13:
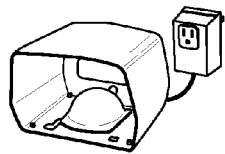
Figure 13:
Figure 13:
Figure 13:
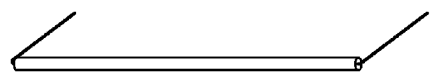
Figure 13:

IR/mechanical/physical sensor (FIG. 11, 13). A pre-installed mechanical/physical activation mechanism can be employed alone or in combination with an electronic sensor. The mechanical physical activation mechanism can be used to override the photo-cell/proximity/optical/IR sensor (FIG. 13).

The automated work station can have a freestanding structure to support the workstation. In an alternative aspect the automated workstation can be mounted into a work counter, or attached to or next to a laminar flow hood.

The automated workstation can have a shield mounted to the work surface area/basin to protect the end user from overspray. In one aspect, the protective shield can have four sides-two sides, back, and top.

Figure 22:
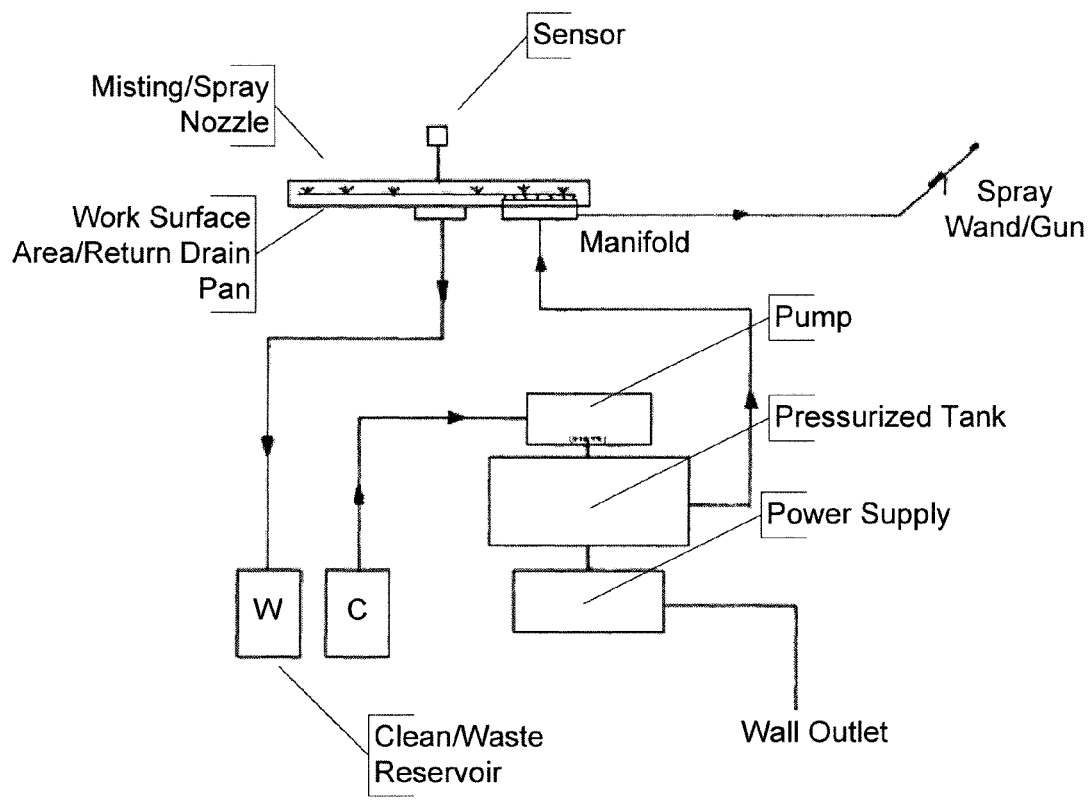
FIG. 22 is a block diagram of the above embodiment of the present invention shown in an operational configuration (to fill in dimensions) capable of disinfecting an animal cage.
Figure 23:
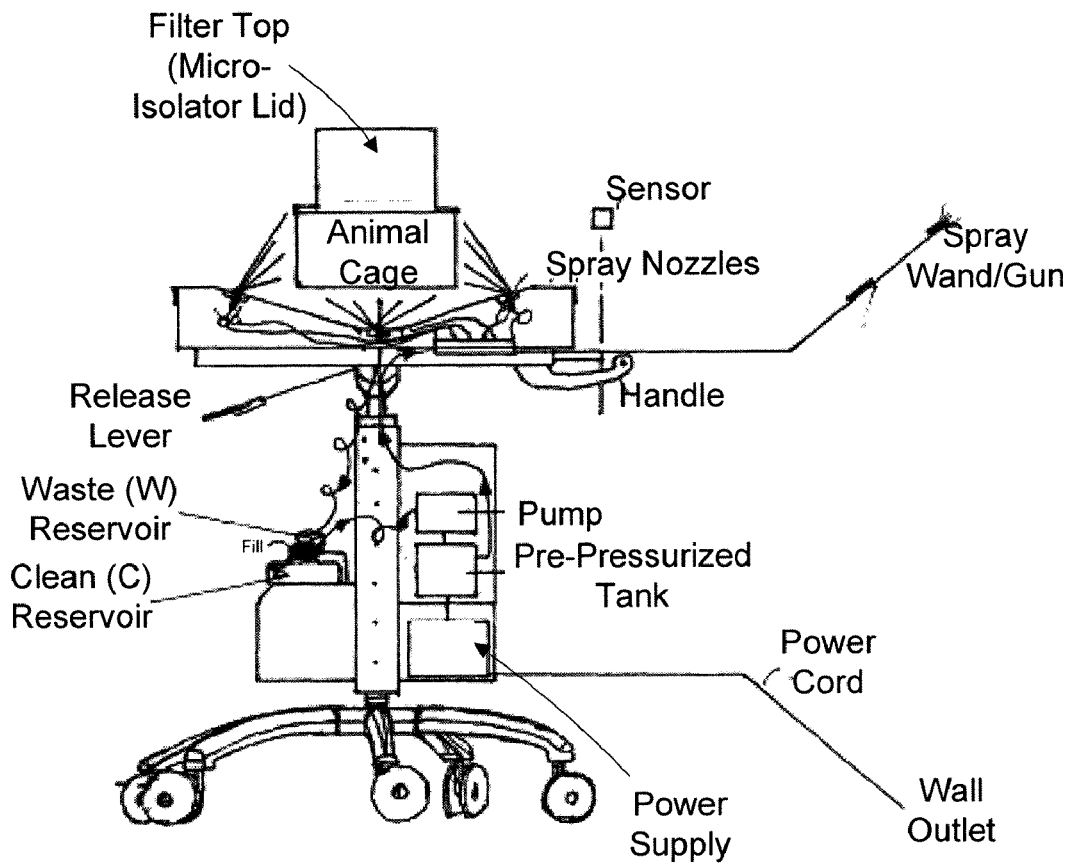
FIG. 23 is a sectional side view of an embodiment of the automated workstation for disinfecting animal cages of the present invention (FIG. 1-22).

A block diagram of the above embodiments of the present invention in an operational configuration capable of disinfecting an animal cage is shown in FIG. 22. Upon connection to wall power and the unit switch turned to "on" position, the pump (FIG. 14) draws disinfectant from the clean reservoir supply bottle (labeled C) and brings the system up to pressure. The pre-pressurized tank (FIG. 15), spray gun/wand (FIG. 20), spray nozzle assembly (FIG. 9), and main trunk line plumbing (FIG. 21) are at working pressure (approximately 60 PSI or higher; range 40-160). The main trunk line plumbing (FIG. 21) is joined via a manifold (FIG. 16), creating a common location to organize multiple lines (FIG. 21) within the fluid system. The spray gun/wand (FIG. 20) can be manually activated at any time by the user via a trigger switch. The presence of a cage (FIG. 24) is detected by a sensor: photocell, proximity, optical, infrared (IR) (FIG. 11), or via manual mechanism: mechanical or physical (FIG. 13) (e.g., a manual override) which triggers the opening of the spray nozzle(s) (FIG. 9) via solenoid valve(s) (FIG. 10) and/or spring loaded internal check valve (FIG. 10). A timed (duration) and/or metered volume (amount) of disinfectant is initiated when a cage is "sensed" via a "object-reflecting", "reflector", "two-piece style" sensor or manually via secondary actuator (FIG. 13), which causes the solenoid valve(s) (FIG. 10) to open the spray nozzle(s) (FIG. 9) disposed within the work surface area (FIG. 3—sectional side view only; FIG. 4—top view only; and FIG. 12—sectional side view of embodiments FIGS. 3, 9, 10, 11, and 24) thereby misting the external four sides and bottom surfaces of the cage (FIG. 12, 24) (e.g., target area). At the end of the pre-determined time (duration) and/or volume (amount), the spray nozzle(s) (FIG. 9) shut-off, thereby terminating the flow pattern of disinfectant (FIG. 9) from the clean reservoir supply bottle (FIG. 6). The cycle is repeated by recognizing the presence of another cage (FIG. 24) via the photo-cell/proximity/optical/IR/mechanical/physical sensor (FIG. 11, 13). A pre-installed mechanical/physical activation mechanism may be employed to override the photo-cell/proximity/optical/IR sensor (FIG. 13). FIG. 23 is a comparable configuration(s) to the block diagram (FIG. 22) termed Pathogen Reduction Misting Station (PRMS) or automated workstation for disinfecting an animal cage.

Any disinfectant that is stable, safe, or inert under pressure can be used in the automated workstation. Disinfectant includes, but is not limited to, chlorine dioxide, Clidox-S® Dilution Disinfectant, Pharmacal Research Labs, Inc., 562 Captain Neville Drive, Waterbury, Conn. 06705), quaternary ammonium chloride, Quatricide TB™, Quatricide PV™, Quatricide PV 15™, Quatricide™, iodine solution, Virkon-S™, potassium peroxymonosulfate (disinfecting/cleansing agent), sulphamic acid (disinfecting/cleansing agent), malic acid (disinfecting/cleansing agent), sodium dodecyl benzene sulphonate (detergent), sodium chloride (disinfecting/cleansing agent), sodium hexametaphosphate (buffering agent), Amaranth dye (indicator colour), Lemon extract (odorant), a detergent, saline, water, or any other commercially available disinfectant(s).

Although the invention has been described with respect to various embodiments, it should be realized that this invention is also capable of a wide variety of further and other embodiments within the spirit and scope of the present invention. The pathogen free transfer station or automated workstation for disinfecting animal cages as disclosed herein can be used in a variety of applications including, but not limited to clean rooms, tissue culture rooms, animal biosafety rooms, physician's office, medical/surgical prep rooms, slaughterhouses, food processing facilities, or any area/room that requires disinfecting ones hands, instruments, or equipment.

Other embodiments and uses will be apparent to one skilled in the art in light of the present disclosures.

The automated workstation for disinfecting an animal cage and methods for disinfecting animal cages can be used in the following environments, including but not limited to, laboratory and SPF environments.

1. Clean rooms which are now used in a variety of industries:
    a. Medical device industry
    b. Biotechnology industry
    c. Semiconductor industry
    d. Pharmaceutical industry
    e. Microelectronics industry (e.g., chip manufacturing)
    f. Life sciences industry
    g. Cosmetic markets
    h. Nanotechnology industry
    i. Defense industry
2. Tissue Culture Rooms for:
    a. Replication-incompetent viruses, uninfected tissues and cell lines
    b. Replication competent viruses and viral DNA
    c. Plant tissue culture (e.g., somatic embryogenesis)
    d. Succulent tissue culture (e.g., produces rare and endangered cacti and succulent plants using in vitro techniques. Research on a growing number of ornamental plants, cut flowers and pot-plants and rare ornamentals like bulb- and caudex forming tropical plants. Induction of tetraploids and basic research in the field of induction of variegation and cristation in in vitro plants
3. Animal Bio Safety Level 2, 3 or 4 (ABSL 2, 3 or 4) Laboratories;
4. Bio Safety Level 2, 3 or 4 (BSL 2, 3, or 4) Laboratories;
5. Physician Offices;
6. Medical/Surgical prep rooms;
7. Slaughterhouses—kill floor and/or meat processing rooms;
8. Food processing facilities, e.g., to clean or remove pathogenic organisms from meat, poultry, fish, seafood, or vegetables;
9. Any area/room that requires disinfecting a person's hands, instruments, or equipment.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

I claim:

1. A method of treating an animal cage, the method comprising:
    detecting, with a sensor, an animal cage containing a live animal within a predefined area relative to a platform; and
    in response to detecting the animal cage, dispensing fluid from a pressurized fluid reservoir through a plurality of nozzles toward at least a portion of exposed surfaces of the animal cage and without endangering the live animal wherein dispensing fluid comprises spraying the fluid at a sufficient rate to disinfect the animal cage in approximately one second.

2. The method of claim 1 wherein dispensing fluid comprises dispensing at least one of chlorine dioxide, Clidox-S dilution disinfectant, quaternary ammonium chloride, Quatricide TB, Quatricide PV, Quatricide PV 15, Quatricide, iodine solution, Virkon-S, potassium peroxymonosulfate, sulphamic acid, malic acid, sodium dodecyl benzene sulphonate, sodium chloride, sodium hexametaphosphate, amaranth dye, lemon extract, a detergent, saline, water, or any combination thereof.

3. The method of claim 1 wherein dispensing fluid through the plurality of nozzles comprises dispensing the fluid through nozzles positioned to spray the fluid onto four external side surfaces and a bottom external surface of the animal cage.

4. The method of claim 1 wherein detecting the animal cage within the predefined area relative to the platform comprises detecting the animal cage in at least one of a laminar flow hood, a biosafety cabinet, or a changing station.

5. The method of claim 1 wherein dispensing fluid through the plurality of nozzles comprises dispensing fluid through at least six nozzles.

6. The method of claim 1 wherein detecting the animal cage comprises using at least one of a proximity sensor, a photocell sensor, an infrared sensor, or a mechanical sensor to detect the animal cage.

7. The method of claim 1, further comprising containing the dispensed fluid with a protective shield positioned between the predefined area and an operator.

8. The method of claim 1, further comprising receiving the animal cage in the predefined area before detecting the animal cage, and wherein the predefined area is exposed to an external environment on at least three sides.

9. The method of claim 1 wherein dispensing fluid comprises dispensing fluid at approximately room temperature.

10. The method of claim 1, further comprising overriding the dispensing via a mechanical activation mechanism.

11. A method, comprising:
    sensing an object within a predefined area relative to a platform, wherein the platform is open to an external environment; and
    dispensing a fluid in response to sensing the object, wherein the fluid is dispensed from a fluid reservoir through a plurality of nozzles directed toward the object in the predefined area, and wherein the fluid is at approximately room temperature when the fluid is dispensed toward the object in the predefined area, and further wherein the fluid is dispensed at a sufficient rate to disinfect the object in approximately one second.

12. The method of claim 11, further comprising collecting the fluid in a basin beneath the predefined area, wherein the basin comprises a generally non-planar surface with a plurality of inwardly sloping surfaces extending from a periphery of the platform toward a drain pan at least proximate to a center portion of the platform, and wherein the inwardly sloping surfaces are positioned to direct the fluid toward the drain pan.

13. The method of claim 11, further comprising collecting the fluid in a waste reservoir after dispensing the fluid.

14. The method of claim 11 wherein dispensing the fluid comprises spraying the fluid as a mist.

15. The method of claim 11 wherein dispensing the fluid comprises spraying the fluid from a spray-gun connected to the reservoir by a flexible hose.

16. The method of claim 11, further comprising:
    receiving input from an activation mechanism; and
    in response to the input, interrupting the dispensing.

17. A method for treating an animal cage at an automated workstation, the method comprising:
    sensing with a sensor when the animal cage is present within a predefined treatment area of the workstation, wherein the animal cage contains a live animal; and
    dispensing fluid from a stored volume of fluid carried by the workstation in response to sensing that the animal cage is within the treatment area, wherein dispensing the fluid comprises spraying the fluid toward at least a portion of the animal cage at a sufficient fluid flow rate to disinfect the animal cage in approximately one second.

18. The method of claim 17, further comprising at least partially containing the dispensed fluid from an external environment with a containment shield.

19. The method of claim 17 wherein the predefined treatment area is sized to contain the animal cage and hands of an operator holding the animal cage, and wherein dispensing the fluid further comprises spraying the fluid toward the hands of the operator.

* * * * *